United States Patent
Krishna et al.

(10) Patent No.: US 8,883,124 B2
(45) Date of Patent: Nov. 11, 2014

(54) USE OF FULLERENES IN PHOTOACOUSTIC IMAGING

(75) Inventors: Vijay Krishna, Gainesville, FL (US); Brij M. Moudgil, Gainesville, FL (US); Benjamin L. Koopman, Gainesville, FL (US); Stephen Grobmyer, Gainesville, FL (US); Iwakuma Nobutaka, Gainesville, FL (US); Qiang Wang, Gainesville, FL (US); Qizhi Zhang, Gainesville, FL (US); Huabei Jiang, Gainesville, FL (US); Parvesh Sharma, Gainesville, FL (US); Amit Kumar Singh, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 970 days.

(21) Appl. No.: 12/740,884

(22) PCT Filed: Oct. 31, 2008

(86) PCT No.: PCT/US2008/082098
§ 371 (c)(1),
(2), (4) Date: Nov. 16, 2010

(87) PCT Pub. No.: WO2009/059215
PCT Pub. Date: May 7, 2009

(65) Prior Publication Data
US 2011/0052495 A1 Mar. 3, 2011

Related U.S. Application Data

(60) Provisional application No. 60/983,961, filed on Oct. 31, 2007.

(51) Int. Cl.
| | | |
|---|---|---|
| *A61B 8/00* | (2006.01) | |
| *G01S 15/00* | (2006.01) | |
| *H04B 1/02* | (2006.01) | |
| *A61K 49/00* | (2006.01) | |
| *A61B 5/00* | (2006.01) | |
| *G01N 21/17* | (2006.01) | |

(52) U.S. Cl.
CPC ............ *A61K 49/00* (2013.01); *A61B 5/0095* (2013.01); *A61B 8/00* (2013.01); *G01N 21/1702* (2013.01); *G01N 2021/1787* (2013.01); *Y10S 977/734* (2013.01); *Y10S 977/842* (2013.01); *Y10S 977/927* (2013.01); *Y10S 977/953* (2013.01)
USPC ............ 424/9.5; 977/734; 977/842; 977/927; 977/953; 367/87; 367/137

(58) Field of Classification Search
CPC ........ A61B 5/0095; A61B 8/00; A61K 49/00; A61K 49/22; G01N 2021/1787; G01N 21/1702
USPC ........... 424/9.5; 977/734, 842, 927, 953, 934; 423/455 B; 367/87, 137
See application file for complete search history.

(56) References Cited

U.S. PATENT DOCUMENTS

| | | | |
|---|---|---|---|
| 5,171,373 A | 12/1992 | Hebard et al. | |
| 5,688,486 A * | 11/1997 | Watson et al. | 424/1.65 |
| 6,123,923 A * | 9/2000 | Unger et al. | 424/9.52 |
| 7,217,404 B2 * | 5/2007 | Ajayan et al. | 423/447.1 |
| 8,313,773 B2 * | 11/2012 | Kim et al. | 424/489 |
| 2005/0070803 A1 | 3/2005 | Cullum et al. | |
| 2005/0175540 A1 | 8/2005 | Oraevsky et al. | |
| 2007/0015978 A1 | 1/2007 | Kanayama et al. | |
| 2007/0015992 A1 | 1/2007 | Filkins et al. | |
| 2007/0197886 A1 | 8/2007 | Naganuma et al. | |
| 2009/0076115 A1 * | 3/2009 | Wharton et al. | 514/410 |
| 2009/0302029 A1 * | 12/2009 | Krishna et al. | 219/678 |

OTHER PUBLICATIONS

"Carbon Nanotube," The American Heritage Dictionary of the English Language, Fourth Edition copyright 2000 by Houghton Mifflin Company. Updated in 2009.*
Ferrante et al., Photochem Photobiol Sci., 2003, 2(7), p. 801-7.*
Jeon et al, Bull. Korean Chem. Soc., 1992, 13, p. 346-348 (abstract).*
Pratt et al., Phys. Chem. Chem. Phys., 2001, 3, p. 1638-1643.*
Ajayan, P.M. et al., "Nanotubes in a Flash: Ignition and Reconstruction," *Science*, Apr. 26, 2002, p. 705, vol. 296, No. 5568.
Krishna, V. et al., "Mechanism of enhanced photocatalysis with polyhydroxy fullerenes," *Applied Catalysis B: Environmental*, 2008, pp. 376-381, vol. 79.
Tam, A.C., "Applications of photoacoustic sensing techniques," *Reviews of Modern Physics*, Apr. 1986, pp. 381-431, vol. 58, No. 2.
Yuan, Z. etal., "Imaging of small nanoparticle-containing objects by finite-element-based photoacoustic tomography," *Optics Letters*, Nov. 15, 2005, pp. 3054-3056, vol. 30, No. 22.
Hertel, I.V. et al., "Giant Plasmon Excitation in Free $C_{60}$ and $C_{70}$ Molecules Studied by Photoionization," *Physical Review Letters*, Feb. 10, 1992, pp. 784-787, vol. 68, No. 6.
Dugan, L.L. et al., "Carboxyfullerenes as neuroprotective agents," *Proc. Natl. Acad. Sci. USA*, Aug. 1997, pp. 9434-9437, vol. 94.
Georgieva, A.T. et al., "Polyhydroxy fullerenes," *J. Nanopart. Res.*, 2013, pp. 1690 (1-18), vol. 15.
Tzirakis, M.D. et al., One-step Synthesis of Fullerene Hydride $C_{60}H_2$ via Hydrolysis of Acylated Fullerenes, *J. Org. Chem.*, 2009, pp. 5746-5749, vol. 74. No. 15.
Zhang, X. et al., "Reaction of $C_{60}$ with Benzocyclobutenol: Expeditious Route to Fullerene Adducts," *J. Org. Chem.*, 1994, pp. 5235-5238, vol. 59.

* cited by examiner

*Primary Examiner* — Michael G Hartley
*Assistant Examiner* — Leah Schlientz
(74) *Attorney, Agent, or Firm* — Saliwanchik, Lloyd & Eisenschenk (57) ABSTRACT

Fullerenes, when irradiated with electromagnetic radiation, generate acoustic waves. A photoacoustic tomography method using a material comprising fullerenes is disclosed that includes irradiating the material with a radiation beam such as a laser. The resultant photoacoustic effect produced by the material is detected by at least one detector. A photoacoustic tomography system using a material comprising fullerenes is also described.

9 Claims, 7 Drawing Sheets

USE OF FULLERENES IN PHOTOACOUSTIC IMAGING

CROSS-REFERENCE TO RELATED APPLICATION(S)

This application is the U.S. national stage application of International Patent Application No. PCT/US2008/082098, filed Oct. 31, 2008, which claims the benefit of U.S. Provisional Patent Application Ser. No. 60/983,961, filed Oct. 31, 2007, and entitled, "Functionalized Fullerenes for Photoacoustic Tomography," the disclosures of which are hereby incorporated by reference in their entireties, including any figures, tables, nucleic acid sequences, amino acid sequences, or drawings.

The subject invention was made with government support under the National Science Foundation, Contract No. EEC9402989. The government has certain rights to this invention.

BACKGROUND

Photoacoustic tomography (PAT) is an emerging non invasive imaging technique, photoacoustic imaging, where the imaging is in three dimensions. A radiation of pulsed electromagnetic waves irradiates a target object causing local thermal expansion and concomitant generation of sound waves. The sound waves can be detected by an ultrasonic detector placed outside of the object being imaged and an image of the object can further be obtained according to the recorded acoustic signals produced by the sound waves. PAT combines the advantages of optical absorption contrast with high resolution of ultrasound. Materials with favorable photoacoustic properties can be used to improve contrast for deep target imaging. Gold nanoshells and some other metallic nanomaterials are being researched for application in PAT, such as that described in U.S. Pat. App. No. 2005/0175540. However, these metallic nanomaterials are inherently toxic, not biodegradable or their fate in the body in not currently completely understood. Accordingly, there remains a critical need for a novel material that can improve photoacoustic properties while being non-toxic, biocompatible and biodegradable.

BRIEF SUMMARY

The subject invention relates to a method of using a material comprising fullerenes for generating acoustic wave by irradiating the material with a radiation of sufficient intensity. The fullerenes can be fullerenes, endohedral fullerenes, substituted fullerenes, functionalized fullerenes or any mixture thereof. The material can have fullerenes secured by carriers or matrices. The material can also be present in aqueous phase.

The subject invention also provides a method of using a material comprising fullerenes for photoacoustic imaging in two or three dimensions, including the steps of: a) irradiating the material with a radiation of sufficient intensity; b) detecting the acoustic waves generated; and c) obtaining an image from the detected acoustic waves.

The subject invention further contemplates a photoacoustic imaging system, comprising a material comprising fullerenes; an object, wherein the material is applied on the object; a light beam source to irradiate the object; and a detector to detect the acoustic waves.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the teachings disclosed herein are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "less than 10" can include any and all sub-ranges between (and including) the minimum value of zero and the maximum value of 10, that is, any and all sub ranges having a minimum value of equal to or greater than zero and a maximum value of equal to or less than 10, e.g., 1 to 5.

In the description of the embodiments, it will be understood that for purposes of the present disclosure, the term "photoacoustic tomography" is given equivalent in meaning to other terms, such as "optoacoustic tomography," "thermoacoustic tomography," "photoacoustic imaging," "optoacoustic imaging," and "thermoacoustic imaging," referring to the same technique. Further, it will be understood that when the term "acoustic waves" is used, it is equivalent in meaning to the terms such as "acoustic signals," "sound signals," "sound," and "ultrasound." In addition, it will also be understood that when a material is referred to as being "on" an object or another material, it can be directly on the object or material, or intervening objects or materials may also be present.

The subject invention involves generating acoustic waves by irradiating a material comprising functionalized fullerenes with electromagnetic radiations above a threshold intensity. Although photoacoustic effect for carbon nanotubes was disclosed by Ajayan et al. ("Nanotubes in a Flash—Ignition and Reconstruction." *Science*, 2002, 296, 705), this phenomenon has never been observed with fullerenes. The invention was enabled by the Inventors' discovery that a material comprising fullerenes could also generate acoustic waves in a manner similar to that observed for carbon nanotubes. The term "fullerenes" defines a general class of molecules that exists essentially in the shape of a three dimensional polyhedron containing from 20 to 1500 carbon atoms, and which comprises carbon atoms as the predominant atomic moiety from which they are composed. The fullerenes herein include but are not limited to fullerenes such as C-28, C-32, C-44, C-50, C-58, C-60, C-70, C-84, C-94, C-250 and C-540. (According to this nomenclature, the fullerene which contains 60 carbon atoms is denoted C-60, the fullerene which contains 70 carbon atoms is denoted C-70, etc.) Also included among the fullerenes for the purpose of the invention are endohedral fullerenes, in which atoms of elements other than carbon reside inside the cage structure of fullerenes. The fullerenes herein also include functionalized fullerenes, in which different functional groups are bonded to the fullerene cage via covalent bonds, or ionic bonds, or Dewar bonds, or Kubas interactions, or mixtures of these bonds. The functional groups can be either inorganic, including but not exclusive to —OH, —Br, —$H_2$, or organic, including but not exclusive to —C(COOH)$_2$ or combinations of organic and/or inorganic. The number of functional groups attached per cage of fullerene can vary from 1 to a majority of the number of carbons in the fullerene cage. Functionalized fullerenes have different physical and chemical properties based on the type and number of functional groups. The fullerenes have dimensions that can be in excess of a nanometer in diameter, and can be considered nanoparticles.

The material comprising fullerenes can include carriers or matrices to secure and orient the fullerenes. In one embodiment, fullerenes can be secured by attaching to the carrier's surface or encapsulated in the matrices. The carriers/matrices can be an organic gas, liquid or solid; an inorganic gas, liquid, or solid; a polymer or polymer composite; water, an aqueous solution or aqueous suspension; a metal or metal alloy; a glass or ceramic; a biological or biologically derived material or any mixture of these materials.

In one embodiment, the material can be in aqueous phase. The material can dissolve or disperse in or be covered by the aqueous phase. It is known to those skilled in the art that because of the nanoscale size of fullerenes, as well as their solubility in water, the terms such as "dissolve," "disperse" and "suspend" can be interchangeable herein, as can be "solution," "dispersion" and "suspension," as in some cases, it is not readily clear that the aqueous phase employed is a true solution or a true suspension. In some embodiments of the invention, as is obvious to one skilled in the art, a solution and suspension are distinct entities. The aqueous phase can also include any chemicals or particles that may or may not interact with the fullerenes. The chemicals or particles may be proteins, contrast agents such as dyes, Gadolinium chelates, or particles including gold, silica, iron oxide and titania.

In a further embodiment of the subject invention, there is provided a method of using a material comprising fullerenes in photoacoustic imaging, comprising the steps of: introducing a material comprising fullerenes on an object; directing a radiation of sufficient intensity onto the material; detecting the acoustic waves; and obtaining an image of the object from the acoustic waves.

The object imaged in various embodiments can be any animate or inanimate samples, such as a cell, tissue or virus. The applications can be directed, not only to medical imaging, but also to other fields such as fluid flow through turbines or porous media, environmental analysis and detection of pathogenic bacteria and viruses.

The material comprising fullerenes can be introduced to the object for example, without limitation, through injection, ingestion or direct application. In one embodiment, the material is introduced through injection on an in vivo object. The material may reach the object locally or contact may take place through systemic distribution. In another embodiment, the material is directly applied on an in vitro object. The material may be in solid, liquid or gaseous phase.

The object can be irradiated with any electromagnetic radiation, such as a laser or a microwave source. The radiation source can be coherent or incoherent. The wavelength of the radiation can range from $10^{-12}$ m to $10^{12}$ m, which includes gamma rays, x-rays, extreme ultraviolet, ultraviolet, visible, infrared, microwave, radio wave, or any combination thereof, depending on the threshold of the fullerenes. For example but not limiting, wavelengths of greater than 740 nm may be used to generate a photoacoustic effect for polyhydroxy fullerenes.

The generated acoustic waves can be detected by any type of transducer, e.g. piezoelectric transducer, capable of sensing acoustic waves and converting them into electric signals. The detected photoacoustic effect can be used to image the object, using known methods within the art of sonic imaging, e.g., finite element reconstruction, to convert the photoacoustic effect to an image that can be analyzed by a user, e.g., a medical technician.

Figure 1:
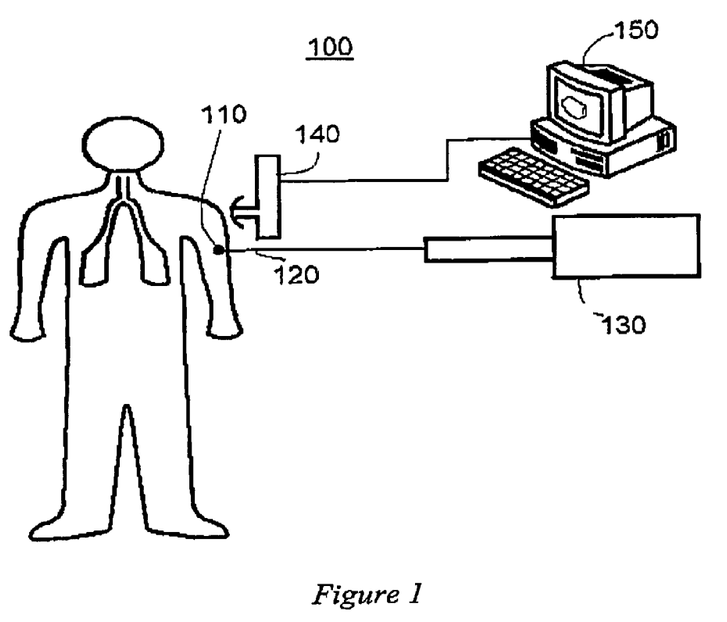
FIG. 1 shows a PAT system, in accordance with an embodiment.
Figure 2:
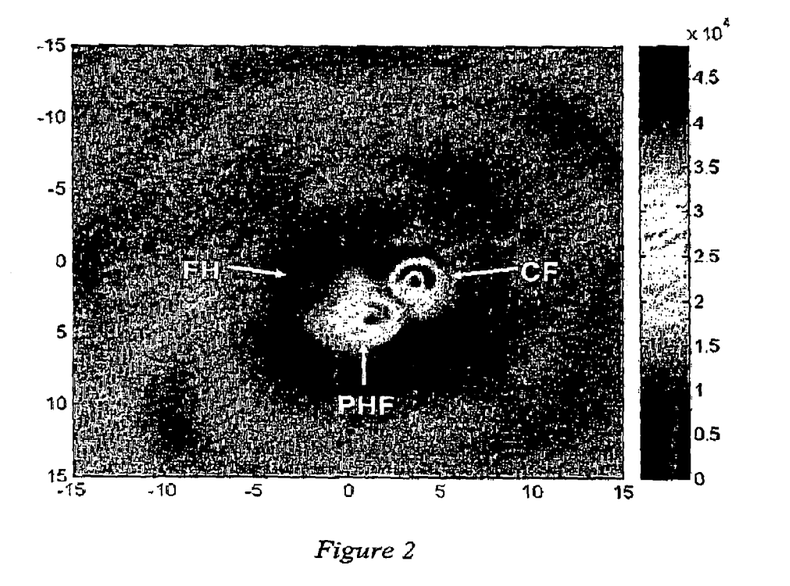
FIG. 2 shows a PAT image of carboxy fullerenes (CF), polyhydroxy fullerenes (PHF) and fullerene hydrides (FH).

The subject invention also encompasses a photoacoustic tomography system, comprising a material comprising fullerenes; an object, wherein the material is applied on the object; a electromagnetic radiation source, such as a light beam, to irradiate the object; and a detector to detect the acoustic waves produced by the object. FIG. 1 shows a PAT system 100, in accordance with an embodiment of the invention. It should be readily apparent to those of ordinary skill in the art that the system 100 shown in FIG. 1 represents a generalized system illustration and that other components can be added or existing components can be removed or modified while still remaining within the spirit and scope of the present teachings.

In particular, the PAT system 100 can include a material comprising fullerenes 110, a radiation source 130, and at least one detector 140. The radiation source 130 can produce a radiation beam 120 with a predetermined wavelength, e.g., 740 nm to irradiate the polyhydroxy fullerenes. The material 110 can contain any fullerenes that produce a photoacoustic effect upon irradiation. Radiation can be provided by a laser. When the material 110 is irradiated with the radiation beam 120 of any wavelength above a threshold intensity, a photoacoustic effect of the material 110 can be triggered. The photoacoustic effect of the material 110 can be detected by the detector 140, which can be an ultrasonic detector. In another embodiment, the system further comprises an imaging device 150 connected to the detector that can use and analyze the detected photoacoustic effect.

In accordance with the teachings disclosed herein, fullerenes, e.g., polyhydroxy fullerenes, can be used with PAT. An advantage of fullerenes over gold nanoshells and carbon nanotubes is that fullerenes have been shown to have antioxidant properties. Moreover, fullerenes have been applied as therapeutics against diseases such as cancer and neurodegenerative diseases. In contrast to gold nanoshells and carbon nanotubes, fullerenes can be subject to clearance from the body.

EXAMPLE

Example 1

Chemicals

Polyhydroxy fullerenes (PHF) were obtained from Bucky-USA (Houston, Tex.) and MER Corp (Tucson, Ariz.). PHF were also synthesized via alkali route as detailed in Krishna et al., *Applied Catalysis B: Environmental* 2008, 79, 376, which is incorporated by reference herein. Pristine fullerenes and carboxy fullerenes (CF) were obtained from BuckyUSA (Houston, Tex.). Fullerene hydride was obtained from MER Corp (Tucson, Ariz.). Chitosan (medium molecular weight) was purchased from Sigma-Aldrich (St. Louis, Mo.). All other chemicals were obtained from Fisher Scientific (Hampton, N.H.).

Example 2

Synthesis of Chitosan-PHF Nanoparticles (CP-0.25 and CP-0.4)

Chitosan-PHF nanoparticles were synthesized by electrostatic precipitation. Chitosan solution was prepared by adding either 25 mg (for CP-0.25) or 40 mg (for CP-0.4) of chitosan to 10 mL of 1% acetic acid. The mixture was stirred for 24 hours to dissolve the chitosan. A volume of 0.9 mL of chitosan solution was added to a microcentrifuge tube. To this, 0.1 mL of PHF (1 mg/mL) was added and mixed several times with the pipette. The mixture was washed by centrifuging at 10,000×g for 10 minutes, followed by removal of the supernatant with a pipette and resuspension of the pellet in deionized water. Three additional washes were carried out. The nanoparticles were characterized by scanning electron microscopy (SEM) (JEOL, JSM-6335F, Peabody, Mass.).

Example 3

Synthesis of Silica-PHF Nanoparticles a) Preparation of Microemulsion

A water-in-oil microemulsion was prepared by mixing 8.85 mg of Triton X-100, 8 mL of n-hexanol and 38.5 mL of cyclohexane, followed by drop-wise addition of 2400 µL of deionized water.

b) Preparation of Dye Conjugate

Dye conjugate was prepared by mixing 6 mg of flouroscein isothiocyanate (FITC) with 14 mg of 3-(aminopropyl) triethoxysilane (APTS) and 1 mL of ethanol for 12 hours in the dark.

c) Synthesis of PHF Encapsulated Dye-Doped Silica Nanoparticles (FCPS)

A volume of 1.25 mL of chitosan (0.25 wt %) was added drop-wise to 50 mL of the microemulsion, followed by addition of 750 µL PHF (10 mg/mL). The mixture was stirred for 2 hours, followed by addition of 125 µL of dye conjugate. After 5 minutes of stirring, 250 µL of tetraethyl orthosilicate (TEOS) and 500 µL of ammonium hydroxide were added. The mixture was stirred for 24 hours in the dark and then precipitated with ethanol. The particles formed during this procedure were washed 2 times with ethanol and 4 times with water. The nanoparticles were characterized by SEM.

d) Synthesis of PHF Coated Dye-Doped Silica Nanoparticles (FSAP)

Dye-doped silica nanoparticles were prepared by adding 25 µL of dye conjugate to 10 mL of the original water-in-oil microemulsion. Silica shells were prepared by addition of 50 µL TEOS, 100 µL APTS and 100 µL of ammonium hydroxide. APTS was added to impart a net positive charge to the silica shells. The dye-doped silica (FSA) nanoparticles were washed twice with ethanol and 4 times with water, and then reacted with 10 mg/mL of PHF to obtain PHF-coated FSA nanoparticles. The FSAP nanoparticles were washed four times with water to remove excess PHF and were characterized by SEM.

Example 4

Photoacoustic Tomography of Functionalized Fullerenes

A mechanical scanning photoacoustic system, with single transducer to collect the acoustic signals, was utilized. The light source was a tunable pulsed Ti:sapphire laser working at 700-950 nm with 10 ns pulse duration, 10 Hz repetition rate and 120 mJ maximum pulse energy. The diameter of the laser beam was expanded to 30 mm with a concave lens. An immersion acoustic transducer with 1 MHz nominal frequency was driven by a motorized rotator to receive acoustic signals from the samples over a range of 360° (3° interval). Thus a total of 120 measurements were performed for each scan.

The scanning plane was adjusted along the z-axis by mounting the rotator and the transducer on a platform driven by a linear stage. The phantom containing the samples and the acoustic transducer were immersed in the water tank, with the phantom at the center of the tank where it was illuminated by the laser. Light-induced electronic signals from the transducer were collected with a receiver and a high-speed PCI data acquisition board. PAT images were reconstructed based on the finite element solution to the photoacoustic wave equation in the frequency domain, which can provide stable inverse solutions in the manner disclosed in Yuan et al. *Opt. Lett.* 2005, 30, 3054.

Phantoms for imaging were constructed using intralipid, India ink, distilled water, and 2% agar powder in the manner disclosed in Tam, A. C., *Rev. Mod. Phys.* 1986, 58, 381. The diameter of the phantom was 25 mm The optical absorption and reduced scattering coefficients of the phantom were 0.007 and 0.5 $mm^{-1}$, respectively. Nanoparticles were embedded in the phantom at a depth of 3 mm.

Figure 3:
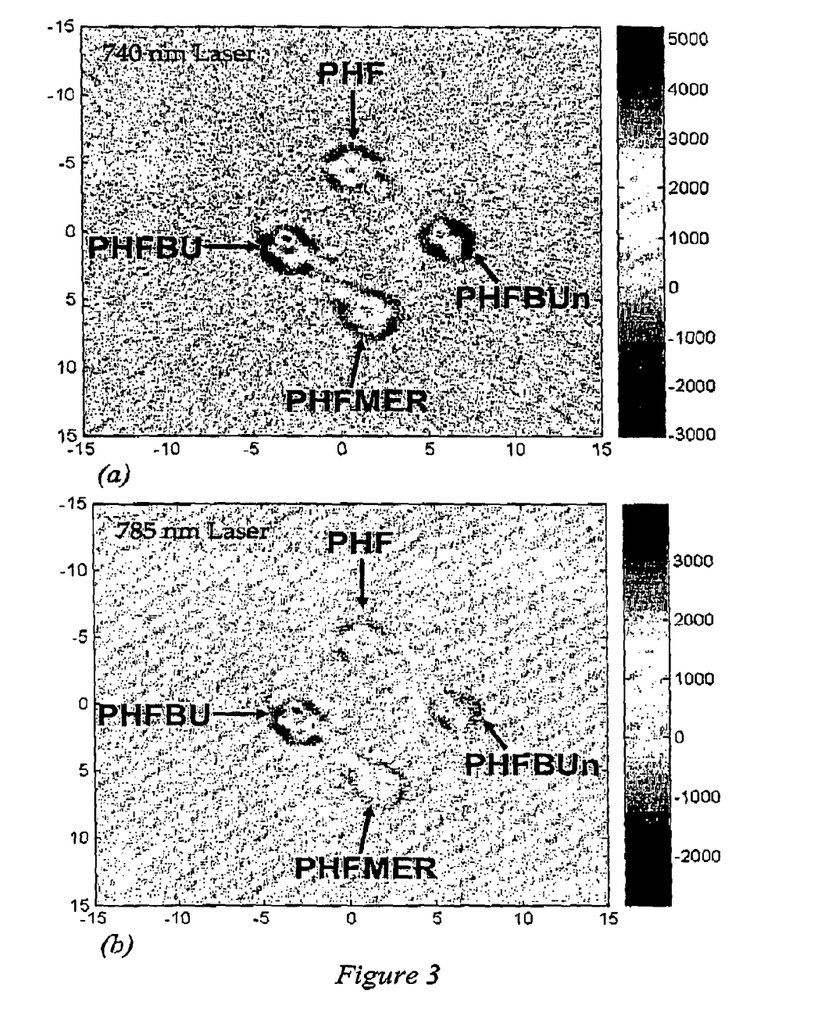
FIG. 3 shows a PAT image of polyhydroxy fullerenes from BuckyUSA (two batches: PHFBU and PHFBUn), MER Corp (PHFMER) and PHF synthesized at PERC. Laser excitation wavelengths for imaging were 740 nm (a) and 785 nm (b). The relative acoustic signal intensity is indicated by scale at the right of each image.

FIG. 1 shows a PAT image of different functionalized fullerenes. Fullerene hydride (FH) exhibits less photoacoustic capability than carboxy fullerene (CF) and polyhydroxy fullerene (PHF). Further experiments were conducted with PHF, as it is water-soluble and is known for its therapeutic properties. PHF can be synthesized with different numbers of hydroxyl groups. To ascertain that various forms of PHF are PAT active, four different samples of PHF were pipetted into the agar phantom and imaged. The four samples of PHF included PHF synthesized as described in Krishna et al., *Applied Catalysis B: Environmental* 2008, 79, 376, two different batches of PHF obtained from BuckyUSA, and PHF obtained from MER Corporation. FIG. 3 indicates that different sources of PHF can be used for PAT imaging. PAT experiments were conducted at two different near-infrared wavelengths, 740 nm and 780 nm. In this study, functionalized fullerenes perform slightly better as PAT contrast agents at the lower wavelength.

Figure 4:
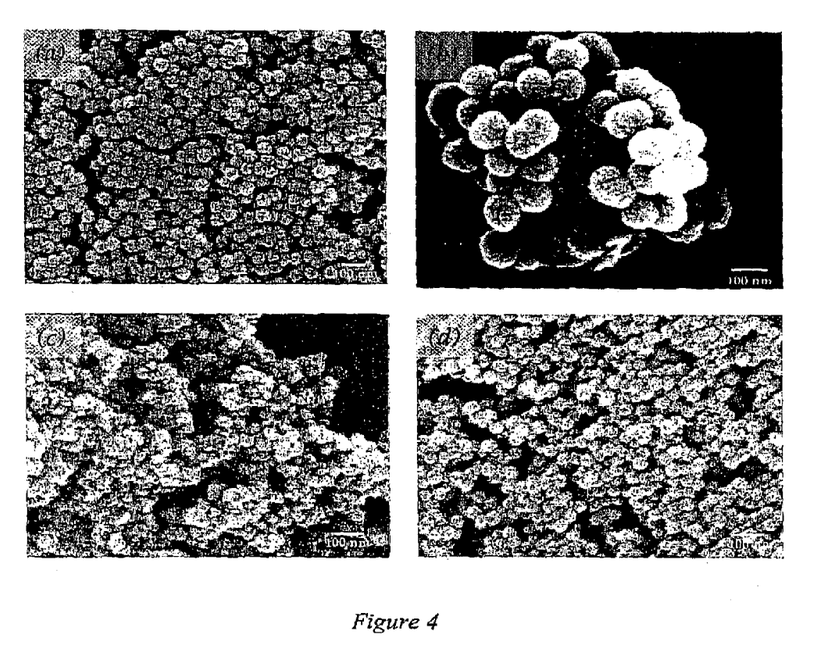
FIG. 4 shows SEM images of (a) PHF encapsulated in chitosan (0.25 wt %), (b) PHF encapsulated in chitosan (0.4 wt %), (c) Fluorescein doped, chitosan-PHF encapsulated in silica and (d) Fluorescein doped silica nanoparticles coated with PHF nanoparticles.
Figure 5:
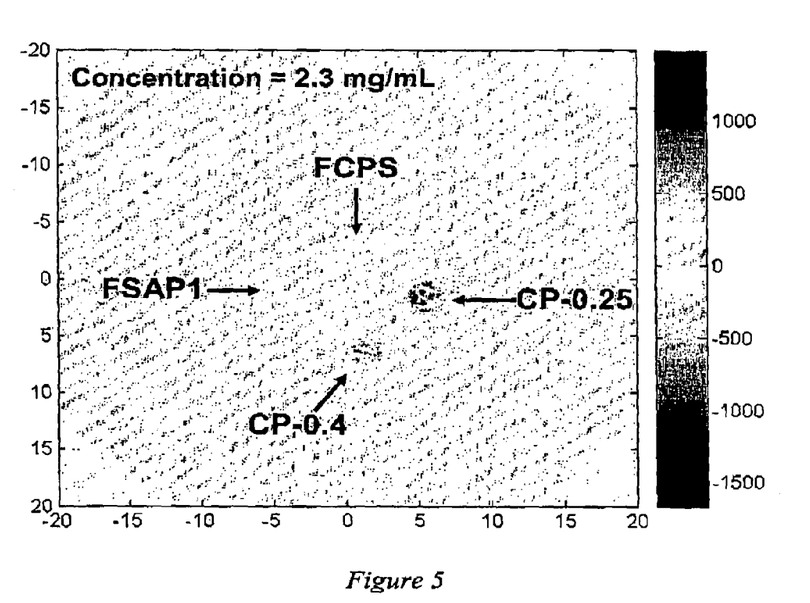
FIG. 5 shows a PAT image of different nanoparticles containing polyhydroxy fullerenes: FCPS—Fluorescein doped, chitosan-PHF encapsulated in silica; CP-0.25—PHF encapsulated in chitosan (0.25 wt %); CP-0.4—PHF encapsulated in chitosan (0.4 wt %); FSAP1—Fluorescein doped silica nanoparticles coated with PHF.

Water solubility of PHF can impose certain limitations for in vivo application, such as high clearance rates. Such limitations can be overcome by encapsulating the PHF in nanoparticles. Nanoparticles containing PHF were synthesized by four different techniques. PHF were either coated on (FSAP) or encapsulated within (FCPS) fluoroscein doped silica nanoparticles. Alternatively, PHF were encapsulated in biodegradable polymer-chitosan (CP-0.25 and CP-0.4). FIG. 4 shows the SEM images of PHF-containing nanoparticles. The average size of the CP-0.25, FCPS and FSAP nanoparticles was 50 nm, whereas CP-0.4 nanoparticles were 100 nm in size. FIG. 5 suggests that CP-0.25 has better PAT contrast than the other three PHF-containing nanoparticles.

Example 5

In vivo PAT

In vivo experiments were carried with mouse tumor model. Six to eight week old BALB/c nude mice (CAnN.Cg-Foxn1nu/Crl) were purchased from Charles River and acclimated for 7 to 10 days. Supplemental estrogen (2 µg of 17β-estradiol valerate/week) was placed subcutaneously at least 1 week prior to tumor implantation. Mice were subcutaneously inoculated with $2\times10^7$ BT474 cells on the abdominal wall. Experiments were conducted 7-10 days following implantation, after the tumors had reached approximately 10 mm in size.

A volume of 30 µL of nanoparticle suspension (10 mg/mL for PHF and 0.45 mg/mL for CP-0.25) was injected into the mouse tumor. The mouse was placed in the water tank on an inclined plane with its head above the water surface. The PAT instrumentation for in vivo experiments was similar to that described for in vitro experiments, except that acoustic signals were collected over 300° range, giving a total of 100 measurements for each trial. PAT images of mouse tumor were obtained before and after injecting nanoparticles.

Figure 6:
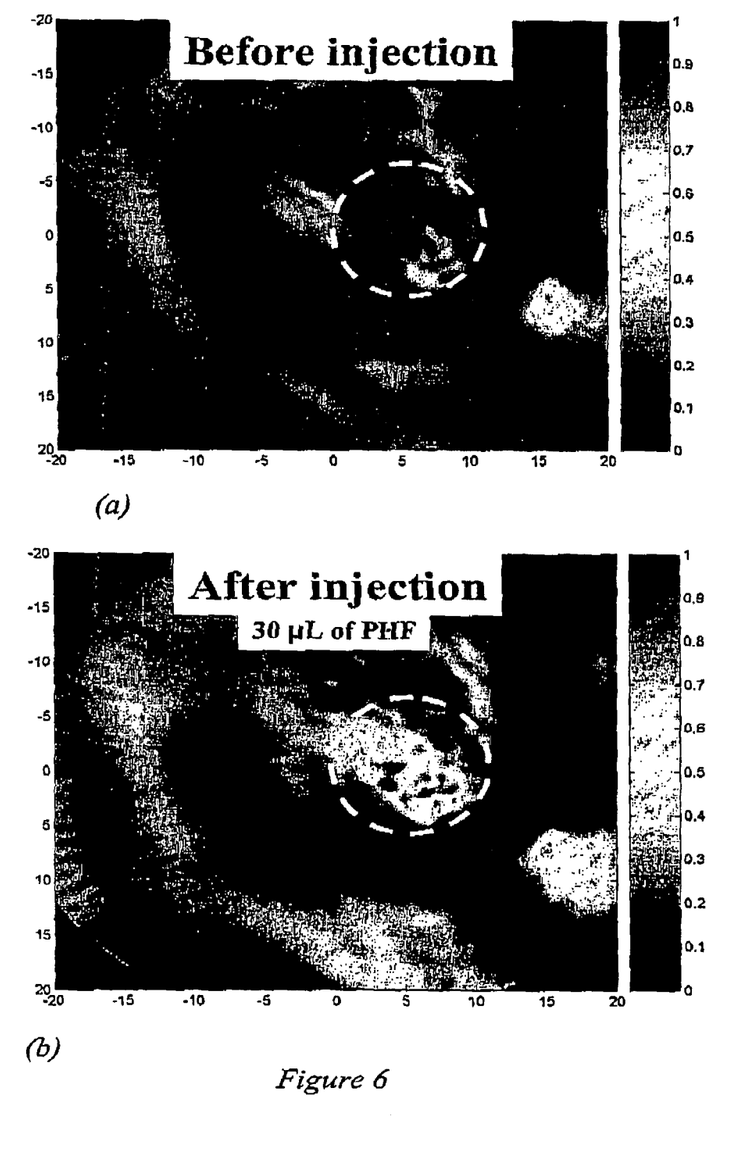
FIG. 6 shows PAT images of mouse tumor before (a) and after (b) intratumoral injection of 30 μL of 10 mg/mL PHF. Following injection of PHF, there is a large increase in PAT signal seen in the region of the tumor (within dashed line). Control intratumoral injection of saline, 30 μL, resulted in no change in PAT signal (image not shown).
Figure 7:
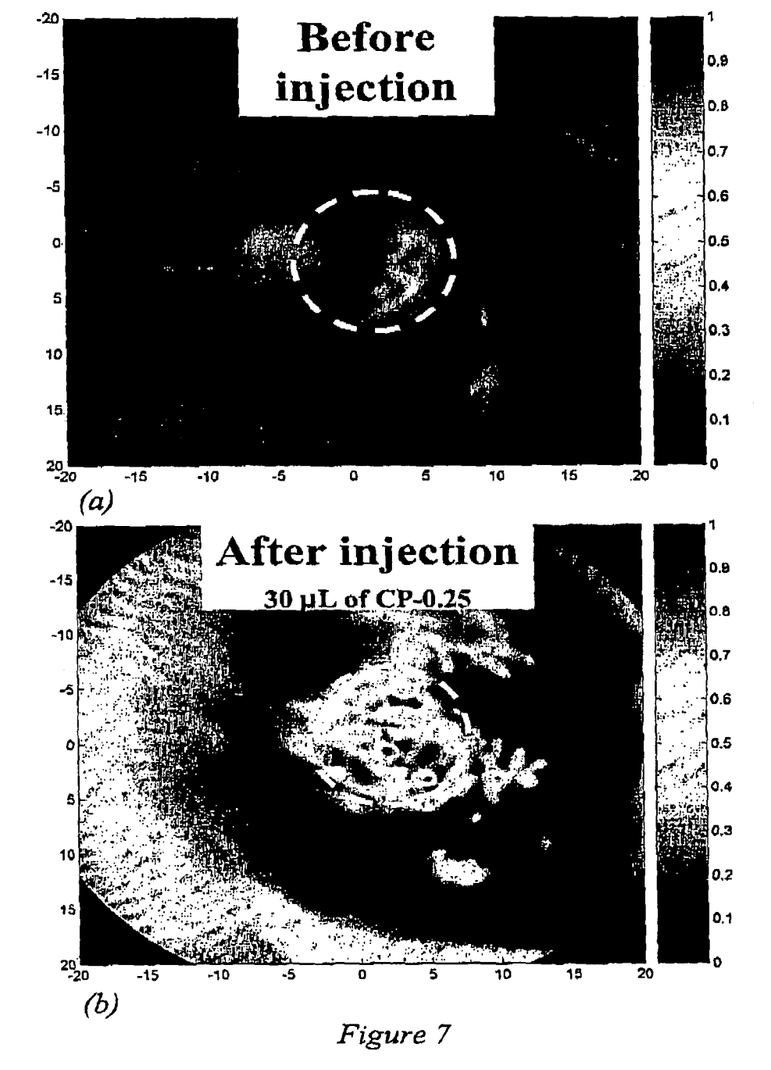
FIG. 7 shows PAT images of mouse tumor before (a) and after (b) injection of 30 μL of 0.45 mg/mL CP-0.25 nanoparticles. Following injection of CP-0.25, there is a large increase in PAT signal seen in the region of the tumor (within dashed line). Control intratumoral injection of saline, 30 μL, resulted in no change in PAT signal (image not shown).

Both PHF and the nanoparticle-encapsulated form of PHF (CP-0.25) demonstrate excellent contrast with the tumor and surrounding non-tumoral tissue and both could easily be imaged in vivo using PAT (FIGS. 6 and 7). Control experiments involving PAT imaging of the tumor following intratumoral injection of 30 µL saline demonstrated no increase in PAT signal (image not shown). The experimental findings demonstrate that PHF and nanoparticles containing PHF can be used as contrast agents for in vivo imaging of tumors (including but not limited to breast cancer, melanoma, and soft tissue sarcomas) using PAT. These findings also demonstrate that PHF and nanoparticles containing PHF can be used as a contrast agent for other types of in vivo deep tissue or intravascular imaging with PAT.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method of generating acoustic waves, comprising the steps of:
   providing functionalized fullerenes wherein said functionalized fullerenes are carboxy fullerenes, hydroxy fullerenes, fullerene hydrides, or any mixture thereof, having at least one $C(COOH)_2$, OH, or hydride group bonded to a fullerene cage; and
   irradiating said functionalized fullerenes with a radiation of sufficient energy to cause the functionalized fullerenes to generate acoustic waves.

2. The material of claim 1, wherein said functionalized fullerenes are dispersed in a carrier or attached to said carrier's surface.

3. The material of claim 2, wherein said carrier comprises an organic gas, liquid or solid; an inorganic gas, liquid, or solid; a polymer or polymer composite; water, an aqueous solution or aqueous suspension; a metal or metal alloy; a glass or ceramic; a biological or biologically derived material; or any mixture thereof.

4. A method of photoacoustic imaging, comprising the steps of:
   introducing functionalized fullerenes wherein said functionalized fullerenes are carboxy fullerenes, hydroxy fullerenes, fullerene hydrides, or any mixture thereof, having at least one $C(COOH)_2$ OH, or hydride group bonded to a fullerene cage on an object;
   directing electromagnetic radiation of sufficient intensity onto said functionalized fullerenes, wherein said functionalized fullerenes generate acoustic waves;
   detecting said acoustic waves; and
   obtaining an image of said object from said acoustic waves.

5. The method of claim 4, wherein said electromagnetic radiation ranges from $10^{31\ 12}$ m to $10^{12}$ m in wavelength and comprises Gamma rays, X rays, Extreme Ultraviolet, Ultraviolet, visible, Infrared, Microwave, Radio wave or any combination thereof.

6. The method of claim 4, wherein said step of introducing comprises injecting on an in vivo object.

7. The method of claim 4, wherein said step of introducing comprises directly applying on an in vitro object.

8. A photoacoustic imaging system, comprising:
   functionalized fullerenes wherein said functionalized fullerenes are carboxy fullerenes, hydroxy fullerenes, fullerene hydrides, or any mixture thereof, having at least one $C(COOH)_2$, OH, or hydride group bonded to a fullerene cage;
   an electromagnetic radiation source to irradiate said functionalized fullerenes, wherein said functionalized fullerenes generate acoustic waves upon irradiation; and
   at least one detector to detect said acoustic waves produced by said functionalized fullerenes, wherein said radiation source and said detectors are configured to generate an image.

9. The system of claim 8, further comprising an imaging device.

* * * * *

UNITED STATES PATENT AND TRADEMARK OFFICE
CERTIFICATE OF CORRECTION

PATENT NO. : 8,883,124 B2  Page 1 of 1
APPLICATION NO. : 12/740884
DATED : November 11, 2014
INVENTOR(S) : Vijay Krishna et al.

It is certified that error appears in the above-identified patent and that said Letters Patent is hereby corrected as shown below:

In the Claims

Column 8,
Line 38, Claim 5 "from $10^{31\ 12}$ m to" should read --$10^{-12}$ m to--.

Signed and Sealed this
Twenty-second Day of September, 2015

Michelle K. Lee
*Director of the United States Patent and Trademark Office*